United States Patent
Borodulin et al.

Patent Number: 6,159,170
Date of Patent: Dec. 12, 2000

[54] UNIVERSAL MECHANICAL DILATOR COMBINED WITH MASSAGING ACTION

[76] Inventors: German Borodulin, 46th Ave., San Francisco, Calif. 94121; Alexander Shkolnik, 485 Dartmouth Ave., San Carlos, Calif. 94070; Maxim Persidsky, 35 Temescal Ter., San Francisco, Calif. 94118

[21] Appl. No.: 08/816,854
[22] Filed: Mar. 13, 1997
[51] Int. Cl.[7] ................................................. A61M 1/00
[52] U.S. Cl. ........................ 601/46; 601/101; 601/97; 606/198; 604/107; 604/108
[58] Field of Search ............... 601/83, 101; 604/104, 604/105, 106, 107, 108, 109; 606/191, 197, 198, 205, 206, 207

[56] References Cited

U.S. PATENT DOCUMENTS

| | | | |
|---|---|---|---|
| 4,607,626 | 8/1986 | Borodulin et al. | 128/43 |
| 4,911,149 | 3/1990 | Borodulin et al. | 128/32 |
| 5,081,985 | 1/1992 | Borodulin et al. | 128/32 |
| 5,133,724 | 7/1992 | Wilson, Jr. et al. | 606/151 |
| 5,318,040 | 6/1994 | Kensey et al. | 128/754 |

*Primary Examiner*—Richard J. Apley
*Assistant Examiner*—Benjamin Koo

[57] ABSTRACT

A universal mechanical dilator combined with massaging action comprises a probe (12) consisting of a two rods (22 and 24), a drive unit (14) and an adapter (16) that connects the probe (12) to the drive unit. The instrument is intended for dilation of the urethra or other ducts of a human body and can operate in three different modes: pure dilation, pure vibration, and dilations combined with vibrations. This is achieved by using the adapter (16) as an adjustable coupling. The probe (12) together with the adapter (16) can be disconnected from the drive unit (14) and used separately as a mechanical manual dilator. At its distal end, the probe (12) has means for connecting replaceable tips (28a, 32a) used for various applications, i.e., urethral, anal, vaginal, etc. The invention also relates to a method of treatment of voiding or an orectal diseases by combining dilations with vibrations. The instrument can also be used for training sphincteric muscles.

7 Claims, 4 Drawing Sheets

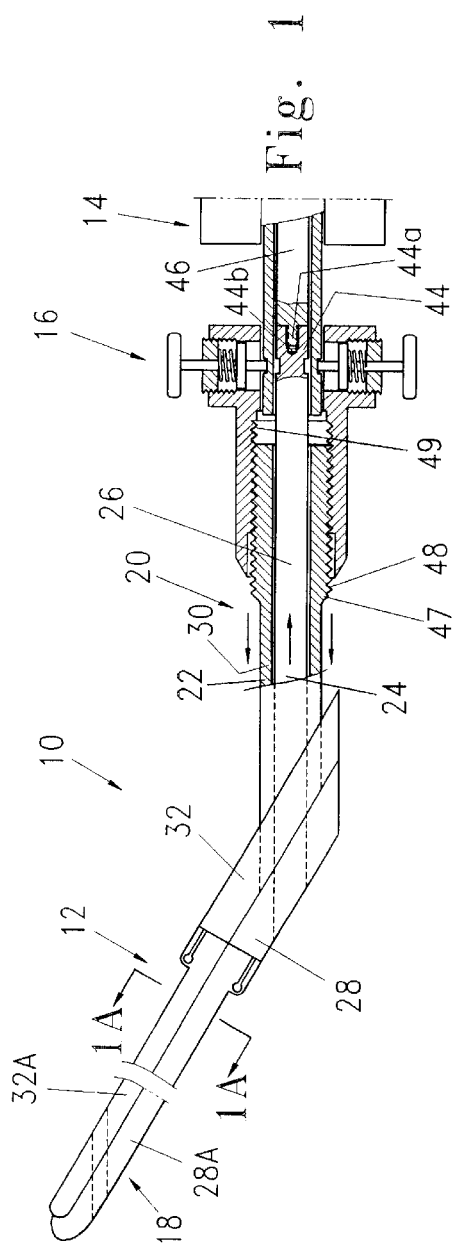
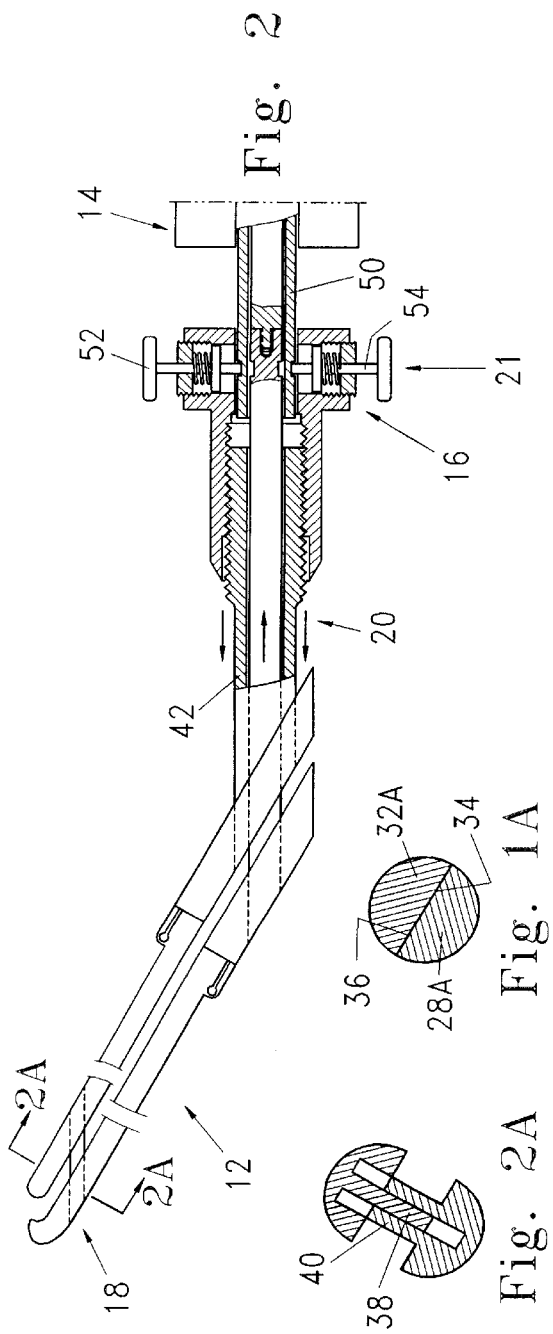

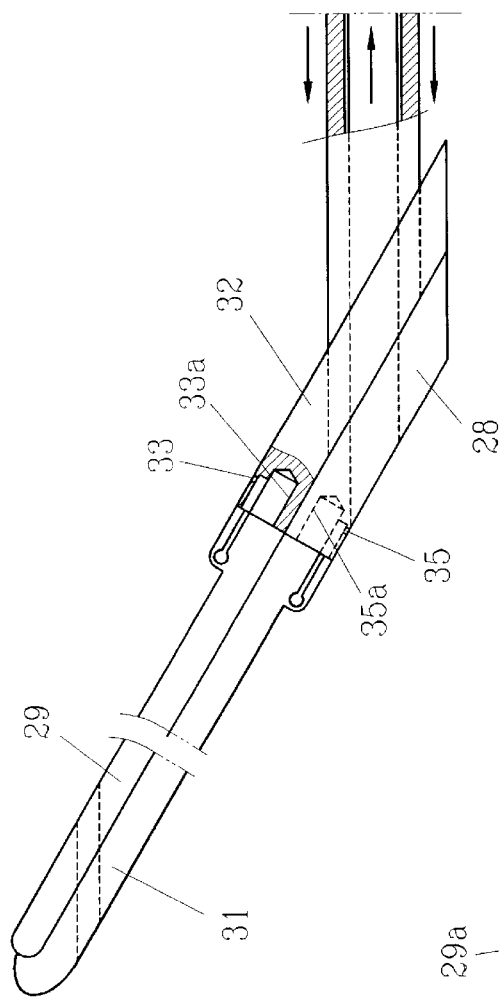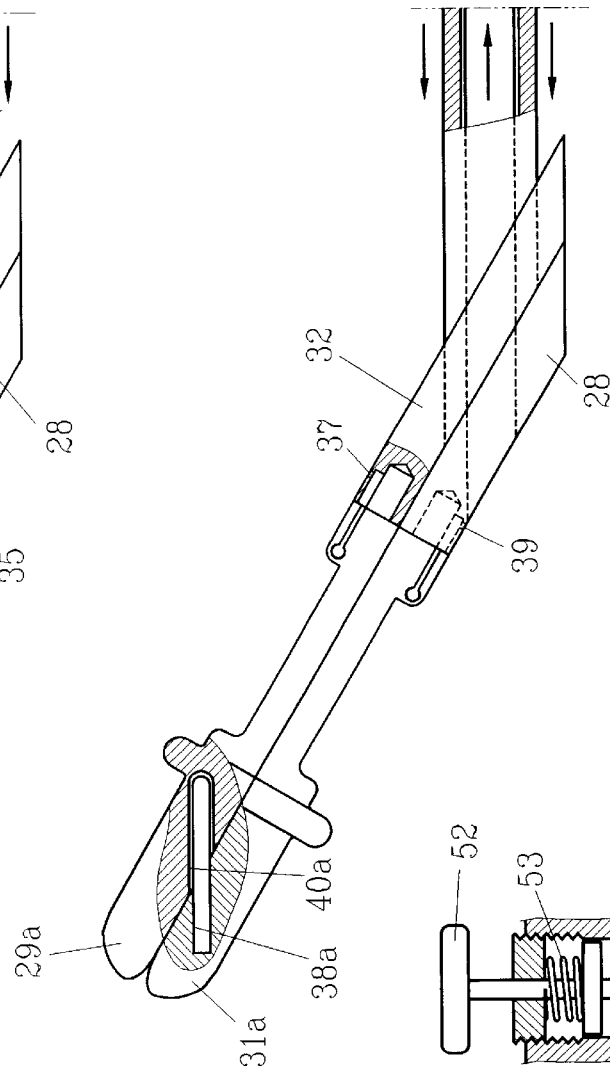

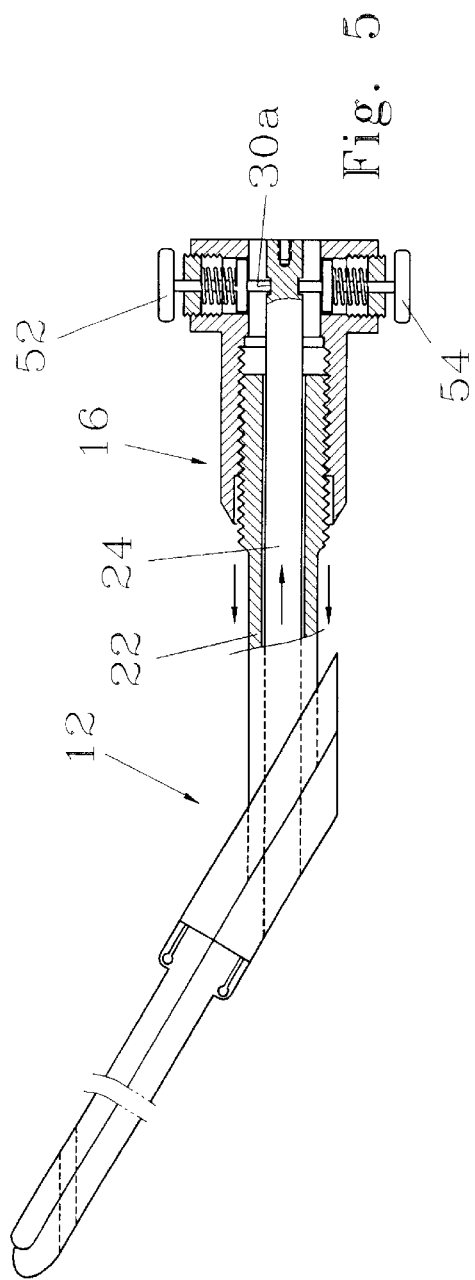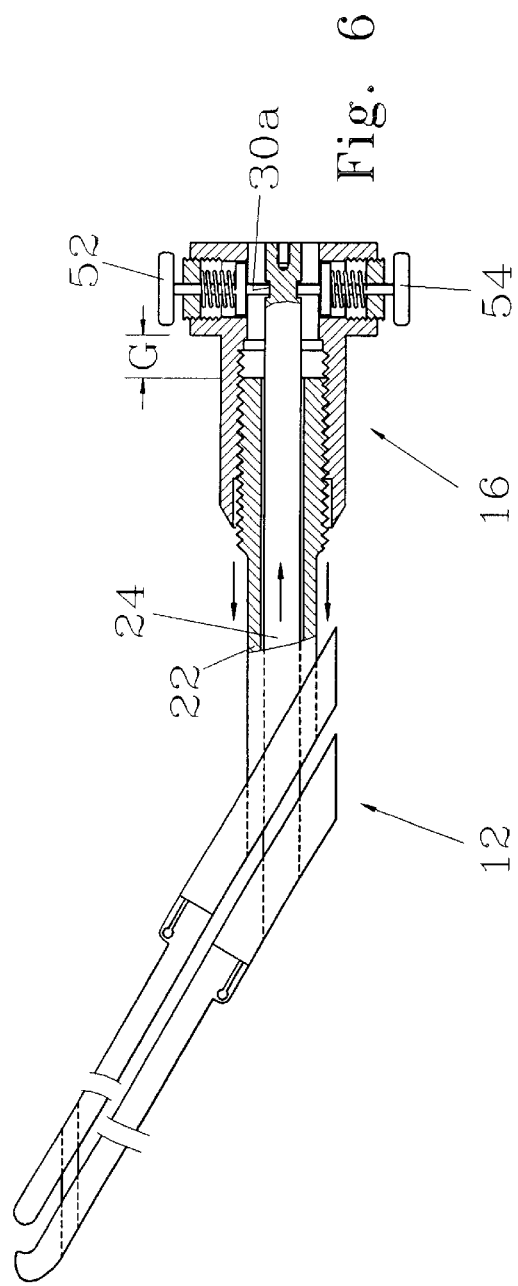

UNIVERSAL MECHANICAL DILATOR COMBINED WITH MASSAGING ACTION

FIELD OF INVENTION

The present invention relates to medical instruments, particularly to a mechanical dilator that combines simple radial mechanical dilation with massaging motions.

BACKGROUND OF THE INVENTION

According to data from the September 1987 issue of the Journal of Urology, 20 million Americans alone suffer from some form of urinary incontinence.

One of the most frequent type of urinary incontinence is the so-called stress incontinence, which is defined as the involuntary loss of urine through the intact urethra as the result of sudden increase in intra-abdominal pressure in the absence of bladder activity. Stress urinary incontinence accounts for roughly 75% of all female urinary incontinence.

Another serious problem which to some extent is neglected, is so-called fecal incontinence. Fecal incontinence is defined as the inability to voluntarily control the passage of feces or gas through the anus and is socially and physiologically debilitating disorder. According to epidemiologic studies close to 2.5% of the general population complain of fecal incontinence. The prevalence rises in the elderly. One of the prime reasons for stress urinary incontinence and fecal incontinence is a breakdown of the urethral and anal sphincteric system as well as the muscles of the pelvic floor. The pathogenesis of stress urinary incontinence and fecal incontinence is multifactorial, and surgery is accompanied by only moderate success. Therefore the conservative type of treatment such as improvement of functional condition of the musles is most commonly used type of treatment.

Another common urinary disorder in females is known as urethral syndrome or frequency nocturia urgency syndrome. Urethral syndrome is a sensory disorder of the lower urinary tract. Its main symptoms are frequency, urgency, dysuria, nocturia, in the absence of bacteriological evidence of urinary infection. The urethral syndrome occurs most often in women and is the most frequent cause for urological consultation of the group. According to national statistics, between 4 and 5 million women suffer from urethral syndrome.

The levator syndrome consists of episodic pain, fullness, and pressure in the rectum and sacrococcygeal area, often aggrevated by sitting. As known, most frequent causes of the urethral syndrome and levator syndrome are the spastic condition of the sphincteric muscles and pelvic floor musculature. Extra-urethral pathology which is revealed in the form of changes in connective tissues between the urethra and vagina. This is expressed in an increased amount of collagenous tissue in the aforementioned area which, in turn, may lead to obstruction. Dilation of the urethra and periodic massage of the spasic muscles is one of the most common methods of conservative treatment for patients suffering from the above-described conditions.

Dilation of the urethra is widely practiced by urologists. To perform a dilation, a doctor is usually uses a set of straight urethral probes with gradually increasing diameters, It is understood that each insertion may increase probability of complications. Therefore the applicants have developed a series of devices for treating voiding dysfunctions.

One such dilator is disclosed in U.S. Pat. No. 4911149 to Borodulin, et al. issued in 1990. It comprises a probe shaped for insertion into urethra and consisting of two rods semi-circular in a cross-section so that in a closed state of the probe they form in a cross section of the probe a complete circle. For dilation to a required diameter the rods are expanded radially outwardly by a camming action of a wedge that is formed on a core element. The core element is placed between the rods and extends in the longitudinal direction of the probe. The core element is connected to a threaded handle that is threaded onto the proximal end of the probe so that rotation of the handle causes axial displacement of the core element together with the wedging cams. As a result of the axial movement of the cams with respect to the rods of the probe is either expanded or contracted.

The use of the aforementioned single adjustable urethral dilator that covers a range of diameters is advantageous. However, the mechanical dilator described in the above patent has a configuration more suitable for dilation of the male urethra.

The therapeutic effect of mechanical stimulation on variety of bodily tissues have been known for nearly a century, and at the present time, low-frequency vibratory massage is successfully being used in various fields of medicine. It is well known that when massage is applied to human tissue, blood circulation intensifies due to the dilation of capillaries. Increased blood flow, in turn, creates a higher consumption of oxygen and nutrients by the muscles. The result is an improved muscle tone, elasticity, an contractile capacity. If the muscle is in the spastic state, the massage produces a relaxation effect on this muscle.

Keeping this in mind, the applicants have developed several vibratory tools for treating voiding dysfunctions. One such tool, i.e., a vibratory device for treating female voiding dysfunctions is described in U.S. Pat. No. 5,081,985 issued to Borodulin, et al. in 1992.

The tool comprises a probe formed of two rods and a drive unit. The drive unit has two output elements which reciprocate simultaneously in mutually opposite directions. Each rod is connected to a respective output drive element. On their inner or mating surfaces the rods have respective cams and curved grooves. During reciprocation of the rods, the cams and grooves interact and thus provide radial expansions of the probe. Additional massaging action is provided by serrations which are formed on the outer surface of the rods and massage the inner walls of the urethra through application of friction forces.

Although this instrument is very efficient in vibratory treatment, it is unsuitable merely for dilation because the dilation occurs only within the range of the vibratory amplitude. Therefore for universal application a urologist should have a set of at least two instruments, i.e., a mechanical dilator for manual dilations and a vibratory tool. The distal ends of the rods are not connected to each other and there is a slight chance that in an expanded state the probes can be slightly shifted with respect to each other in a transverse direction. Another disadvantage of the tool disclosed in the aforementioned US Patent is that at the proximal end of the probe, where the probe is connected to the handle, the ends of both rods are rigidly clamped so that, when the probe is expanded, concentration of stress occurs at the aforementioned point of connection. This is because in this point the rods are inclined with respect to the longitudinal axis of the probe and therefore are deformed. At least this limits the range of expansion.

Another vibratory urethral tool is disclosed in U.S. Pat. No. 4,607,626 issued in 1986 to Borodulin et al. Since the distal ends of the rods are pivotally connected to each other, the urethra cannot be expanded uniformly and the maximum dilation is ensured only in the intermediate portion of the probe. The tool of this type has the same limitations of application as the tool of U.S. Pat. No. 5081985, except for a curved shape that conforms the shape of the urethra.

Furthermore, universal mechanical dilators which can be used for dilation of various narrowings (functional or organic obstructions) with simultaneous vibratory massaging action and training of sphincteric muscles are unknown. Therefore sets of different instruments are required for treating these disorders.

OBJECTS OF THE INVENTION

In view of the above, it an object of the invention to provide a universal mechanical dilator for different medical applications that selectively combines simple radial mechanical dilation with vibratory massaging action, allows operation in one of three operation modes such as dilation, vibration, or dilation combined with vibration, is simple and inexpensive to manufacture, and ensures an increased range of dilation diameters.

These and other objects and features of the invention will become more apparent after consideration of the ensuing description with the accompanying drawings.

BRIEF DESCRIPTION OF THE DRAWINGS

FIG. 1 is a longitudinal sectional view of the combined vibratory instrument and dilator of the present invention, the parts being shown in a closed state of the probe.

FIG. 1A is a cross-sectional view along line IA—IA of FIG. 1.

FIG. 2 is the same view as in FIG. 1 but with parts in an expanded state of the probe.

FIG. 2A is a cross-sectional view along line IIA—IIA in FIG. 2.

FIG. 3 is a fragmental view of the instrument with replaceable distal ends of the probe, the parts being shown in the closed state of the probe.

FIG. 3A is a view similar to FIG. 3 but illustrating replaceable distal ends of an anorectal probe.

FIG. 4 is an enlarged fragmental view illustrating the construction of a lock pin.

FIG. 5 is a longitudinal partially-sectional view illustrating an embodiment of the instrument with the drive unit disconnected, parts being shown in the closed state of the probe.

FIG. 6 is the same view as in FIG. 5 but with the parts in the dilated position of the probe.

Figure 7:
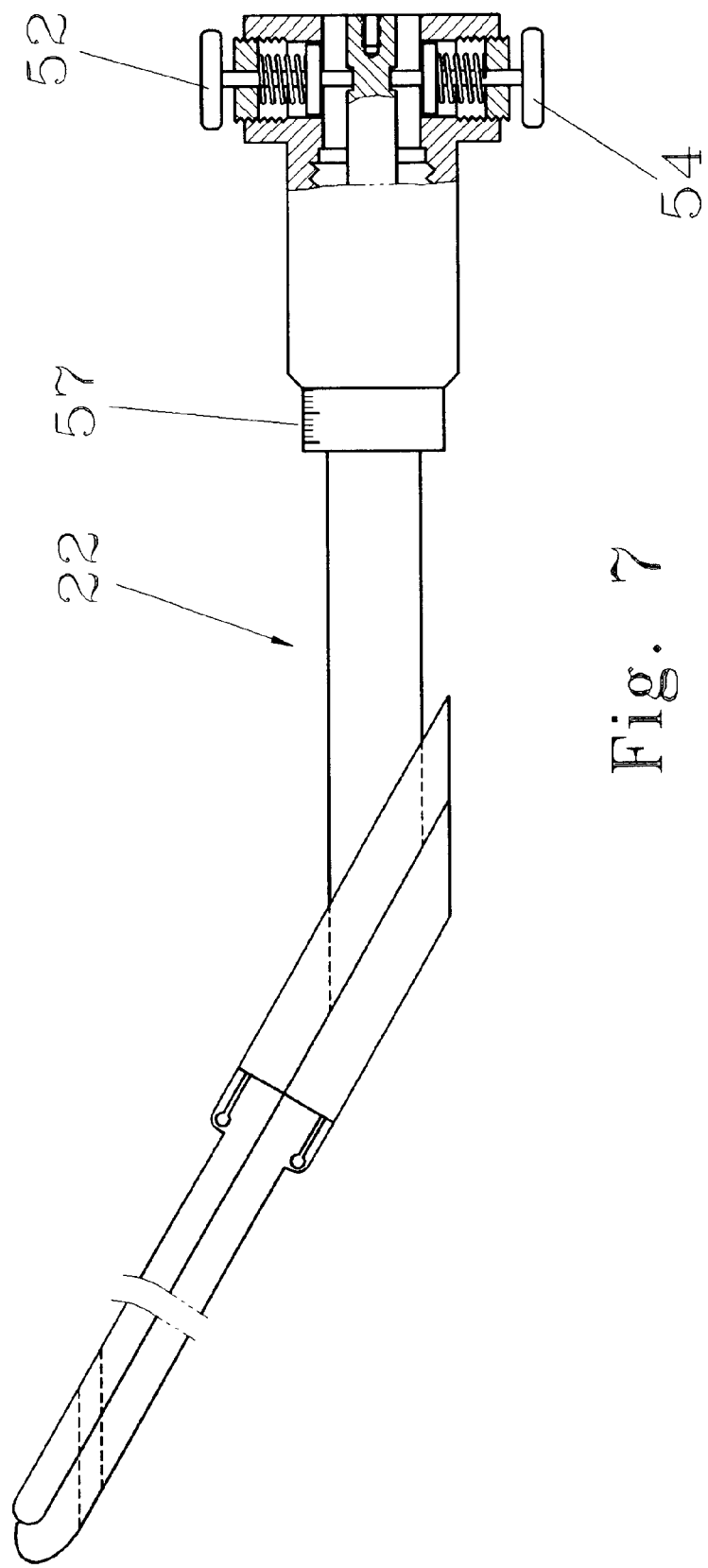
FIG. 7 is a fragmental view of the probe with adapter showing the dilation scale.

DETAILED DESCRIPTION OF THE COMBINED DILATOR AND VIBRATORY INSTRUMENT FOR TREATINGUREATHAL AND ANAL DISORDERS

FIG. 1 is a longitudinal sectional view of the combined vibratory instrument and dilator of the present invention, the parts being shown in a closed state of the probe. FIG. 2 is a view similar to that of FIG. 1 with the parts shown in an expanded state of the probe.

The instrument 10 consists of three main parts, i.e., a probe 12, a reciprocating or vibratory drive unit 14, and an adapter 16 for connecting probe 12 to vibratory drive unit 14.

The longitudinal direction of the front or distal end 18 of probe 12 intersects the longitudinal direction of the proximal portion 20 of the probe at a certain angle. This angle may be within the range of 10 to 70°. The front or distal end 18 of the probe is the portion of the probe that is to be inserted into the patient's urethra or other orificium, and the proximal portion 20 is used for connection to adapter 16.

Probe 12 consists of two rods, i.e., a shorter rod 22 and a longer rod 24. The rods are similar in their configuration in that each of them corresponds to the configuration of probe 12, i.e., shorter rod 22 consists of a straight portion 26 and a bent portion 28 that is arranged at an angle of 10 to 70° to the straight portion 26. Similarly, longer rod 24 consists of a straight portion 30 and a bent portion 32 arranged at the same angle as the respective portions of the shorter rod.

As shown in FIG. 1A which is a cross-sectional view along line IA—IA of FIG. 1, portions 28A and 32A of both rods have semicircular cross sections that form in a closed state of the probe a full circle. Inner surfaces 34 and 36 of rod portions 28 and 32 are flat and mate each other.

As shown in FIG. 2A, which is an enlarged fragmental view along lines IIA—IIA of FIG. 2 illustrating auxiliary guide means on distal end 18 of the probe of FIG. 1, proximal rod portions 28 and 32 have on their mating surfaces 34 and 36 overlapped guides 38 and 40 that are constantly overlapped even in the position of maximum dilation of the probe so that rods 22 and 24 are always protected from being shifted in the direction perpendicular to the longitudinal direction of the probe. As can be seen from FIG. 2, overlapped guides 38 and 40 are inclined to the longitudinal axes of the bent portions of the probe and has the same direction as the straight portions of the probe.

Straight portion 26 of shorter rod 22 may have a circular cross section and has a through longitudinal central opening 42. Straight portion 30 of longer rod 24 may have a circular cross section and is slidingly inserted into opening 42.

A proximal end 44 of straight portion 30 of longer rod 24 has on its outer surface an annular groove 30a the purpose of which will be explained later in conjunction with FIGS. 5 and 6.

A proximal end 44 of straight portion 30 of longer rod 24 is connected, e.g., by threaded opening 44a to threaded projection 44b of a first output member 46 of reciprocating or vibratory drive unit 14.

A proximal end 47 of the straight portion of short rod 22 is connected, e.g., by thread 48 to inner thread 49 of adapter 16. The latter, in turn, is connected to a second output member 50 of drive unit 14.

Rods 22 and 24 can be made of a medically-acceptable material suitable for sterilization, e.g., of stainless steel, or the probe can be made of plastic and be disposable.

As shown in FIGS. 3 which illustrates distal end 18 of the probe in a close state, each bent portion 28 and 32 of shorter rod 22 and longer rod 24, respectively, may have respective disposable parts 29 and 31. The disposable parts constitute those parts of the probe that are to be inserted into the patient's urethra. They can be supplied in a sterilized state and packed in a sealed package (not shown).

In the embodiment shown in FIGS. 3, disposable parts 29 and 31 are connected to parts 32 and 28 of the bent portions of the probe by means of spring-loaded latches 33 and 35. The springing properties are provided by forming longitudinal slots 11 and 13 in the rear part of each disposable portion. Disposable parts 29 and 31 also have at their rear ends projections 29a and 31a. On the other hand, front ends of bent portions 28 and 32 have openings 35a and 33a with through transverse openings 37 and 39. When disposable parts 29 and 31 are to be connected to the probe, projections 29a and 31a are inserted into openings 33a and 35a until latches 33 and 35 snap into transverse openings 37 and 39. For disconnection of the disposable parts, it is necessary to squeeze their slotted ends so that latches 33 and 35 will come out of transverse openings 37, and 38 and projections 29a and 31a can be withdrawn from openings 33a and 35a.

FIG. 3A is a view similar to FIG. 3 but illustrating replaceable distal ends of an anorectal probe. As can be seen from this drawing, disposable parts 29a and 31a are larger in diameter than respective parts 29 and 31. The connection elements are identical to those of FIG. 3, but guide portions 38a and 40a are longer in view of a larger dilation diameter.

As shown in FIGS. 1 and 2, adapter 16 has a shape of a sleeve with an enlarged-diameter rear portion 19 that incorporates a locking mechanism 21. The locking mechanism consists of two identical spring-loaded lock pins 52 and 54 that are arranged in diametrically opposite positions. Since both lock pins are identical, only of them (i.e., lock pin 52) will now be described with reference to FIG. 4.

As shown in FIG. 4, lock pin 52 is spring-loaded by a spring 53 so that it normally urged radially inwardly. On the other hand, second output element 50 has an annular groove 55 on its outer surface, so that when second output element 50 is inserted into adapter for the connection of probe 12 to drive unit 14, the ends of rods 52 and 54 snap into annular groove 55. As a result, second output element 50 will perform its reciprocation together with shorter rod 22.

Reciprocatory or vibratory drive unit 14 may be a conventional commercially available device, such as a drive unit for an electric knife with two blades that reciprocate in opposite directions. Unit 14 includes a housing with an electric motor (not shown) and a supply cord for connection to a conventional electric power source (not shown), preferably s storage battery.

As shown in FIGS. 5 and 6, probe 12 of the instrument of FIG. 1 can together with adapter 16 be disconnected from drive unit 14. For this purpose, lock pins 52 and 54 are pulled radially outward for disengagement from annular groove 55, and adapter 16 is rotated for several revolutions for displacing the ends of lock pins 52 and 54 from alignment with groove 55. The lock pins are then released, and drive unit 14 is disconnected from the probe by unscrewing threaded end 44a from inner thread 44b. Adapter 16 is then rotated in the opposite direction until the ends of lock pins 52 and 54 snap into annular groove 30a on the outer surface of longer rod 24. As a result, adapted 16 and longer rod 24 form an integral unit and the rotation of adapter 16 will shift longer rod 24 with respect to shorter rod 22. Such disconnection converts the instrument into a conventional non-vibrational urethral dilator.

As shown in FIG. 7 which is a fragmental view of the probe with the adapter, a scale 57 is provided on the outer cylindrical surface at proximal end 47 of shorter rod 22. The reading of the scale are made with respect to the front end face of adapter 16.

When the probe is assembled for manual dilation into a configuration shown in FIGS. 5 and 6, lock pins 52 and 54 will protrude radially downward under the effect of their respective springs so that their inner ends snap into annular groove 30a at the proximal end of longer rod 24.

Operation of the Instrument in the Dilation Mode without Massaging Action but with the Drive Unit Connected In some treatment procedures, the patient's orificium, e.g., the urethra, must first be dilated and only after dilation be subjected to vibratory treatment. For this purpose the instrument can be used in the form shown in FIGS. 1 and 2 so that after the completion of dilation the instrument will be immediately ready for the vibratory treatment.

In order to use instrument 10 in the pure dilation mode of operation with drive unit 14 installed but switched off, probe 12 and adapter 16, i.e., the dilator shown in FIGS. 5 and 6, has to be connected to drive unit 14. For this purpose, lock pins 52 and 54 are withdrawn from annular groove 55, threaded end 44a of first output drive member 46 is screwed into inner thread 44b at the end of longer rod 24. When threaded element 44a is connected to the threaded element 44b, annular groove 30a is aligned with the position of lock pins 52 and 54, so that when the lock pins are released, they snap into groove 30a. As a result, second output member 50, adapter 16, and shorter rod 22 form an integral unit that will move as a whole together with second output member 50. Similarly, longer rod 24 forms an integral unit together with first output member 46 and reciprocates with it.

In the case the probe has disposable or reusable distal ends such as those shown in FIG. 3 or FIG. 3A, disposable ends 29 and 31 are connected by inserting projections 29a and 31a into respective openings 33a and 35a until latches 33 and 35 snap into respective transverse openings 37 and 39. As shown in FIG. 3A, which is a view similar to FIG. 3 but illustrating replaceable distal ends of an anorectal probe, replaceable ends may be used for changing diameters or configurations at the working ends of the probes.

The urologist is then inserts instrument 10 into the patient's urethra or some other orificium of a human body (not shown) in accordance with a procedure known in the art, and then dilation is initiated by rotating adapter 16 in the direction that provides threading of thread 48 of shorter rod 22 into inner thread 49 of adapter 16 so that inner bent portion 28 of shorter rod 22 begins to move away from bent portion 32 of longer rod 24 (FIG. 2). As a result, the distal bent end of probe 12 is expanded, and the urethra is dilated to its physiological size. At the same time, guide projection 38 slides within guide groove 40, so that the rods at the distal end of probe 12 are prevented from disconnection.

Upon completion of the dilation of the urethra to its physiological size, adapter 16 is rotated in the opposite direction, so that the rods are closed and the vibratory treatment can be initiated by switching on vibratory drive unit 14.

In the event the mechanical dilator of the invention is used for treating anorectal dysfunctions with the use of replaceable ends 29a and 31a, the dilator is used in the same manner as has been described above with reference to the urethral treatment, with the exception that the dilator is inserted to an anal opening of the patient by a proctologist, the probe is expanded to the physiological size of the anal opening, and the vibrations are applied to the walls of the anal opening.

Operation of the Instrument in the Dilation Mode Combined with Vibratory Massaging Action In order to use instrument 10 for dilation combined with vibratory action, instrument 10 must be connected to drive unit 14 in the same manner as described above in connection with FIGS. 1 and 2.

In the case of urological use, the urologist is then inserts instrument 10 into the patient's urethra (not shown) in accordance with a procedure known in the art of urology, and then the motor (not shown) of reciprocatory drive unit 14 is switched on. Since rods 22 and 24 are connected to respective output members 50 and 46, they begin to reciprocate with respect to each other with a small amplitude (e.g., from 0.1 mm to 2.00 mm) and with low frequency of vibrations (e.g., from 1 Hz to 200 Hz).

Simultaneously with vibrations, dilation is initiated by rotating adapter 16 in the direction that provides threading of thread 48 of shorter rod 22 into inner thread 49 of adapter 16 so that inner bent portion 28 of shorter rod 22 begins to move away from bent portion 32 of longer rod 24. As a result, the distal bent end of probe 12 is expanded and the urethra is dilated and is subjected to vibratory massaging action.

If necessary, the dilation may be discontinued and vibratory treatment can be continued for a required period of time at any point of dilation.

Upon completion of the treatment, the drive motor is switched off, and adapter 16 is rotated in the opposite direction, so that the rods are closed and the probe can be removed from the urethra.

In the event the mechanical dilator of the invention is used for treating anorectal dysfunctions, the dilator is used in the same manner as has been described above with reference to the urethral treatment, with the exception that the dilator is inserted to an anal opening of the patient by a proctologist with replaceable ends 29a and 31a of a larger diameter, and the vibration is carried out simultaneously with the dilation.

Operation of the Instrument in Pure Vibratory Mode

In order to use instrument 10 in the pure vibratory mode, i.e., without manual dilation, the instrument should be connected to drive unit 14 in the manner describe above.

In the case of urological use, the urologist is then inserts instrument 10 into the patient's urethra (not shown) in accordance with a procedure known in the art of urology, and then vibratory treatment is initiated by starting drive unit 14. As a result, inner bent portion 28 of shorter rod 22 and bent portion 32 of longer rod 24 begin to vibrate with respect to each other in the direction of dilation of the probe. In fact, such a mode is a dilation in which the bent portion of probe 12 is expanded to a magnitude equal to the amplitude of the vibrations in the dilation with vibration.

Such a treatment is required for patients suffering from different types of voiding dysfunctions such as stress urinary incontinence, urethral syndrome, etc. Upon completion of the procedure, the drive unit is switched off, and the probe can be removed from the urethra.

In the event the mechanical dilator of the invention is used for treating anorectal dysfunctions, the dilator is used with replaceable ends 29a and 31a in the same manner as has been described above with reference to the urethral treatment, with the exception that the dilator is inserted to an anal opening of the patient by a proctologist.

In all vibratory modes of operation, the mechanical dilator is used with a low-frequency vibrations, e.g., within the range 1 to 200 Hz and with an amplitudes selected, depending on the application conditions, within the range of 0.1 mm to 3 mm.

Operation of the Instrument as a Manual Dilator (without the Drive Unit)

For operation in this mode, probe 12 of the instrument of FIG. 1 should be disconnected from drive unit 14 together with adapter 16. For this purpose, lock pins 52 and 54 are pulled radially outward for disengagement from annular groove 55, and adapter is rotated for several revolutions for displacing the ends of lock pins 52 and 54 from alignment with groove 55. The lock pins are then released, and drive unit 14 is disconnected from the probe by unscrewing threaded end 44a from inner thread 44b. Adapter 16 is then rotated in the opposite direction until the ends of lock pins 52 and 54 snap into annular groove 30a on the outer surface of longer rod 24. As a result, adapted 16 and longer rod 24 form an integral unit and the rotation of adapter 16 will shift longer rod 24 with respect to shorter rod 22. Such disconnection converts the instrument into a conventional non-vibrational urethral dilator.

Dilation is carried out by rotating adapter 16 so that inner thread 49 engages outer thread 48 of shorter rod 22. As adapter 16 moves axially forward with respect to shorter rod 22, lock pins 52 and 54 pull longer rod 24 together with the adapter due to engagement of the inner ends of lock pins with annular groove 30a on the outer surface of the longer rod. As a result, as shown in FIG. 6, the probe is expanded.

For all embodiments and modes of operation, it is important that the distance G selected so that at the moment of full dilation, guided elements 38a and 40 remain engaged.

The degree of dilation is observed by using scale 57 (FIG. 7) with respect to a front end face 16a of adapter 16.

SUMMARY, RAMIFICATIONS, AND SCOPE

Thus, it has been shown that the universal female mechanical urethral dilator of the present invention selectively combines in itself simple radial mechanical dilations with vibratory massaging motions, allows operation in one of three operation modes such as dilation, vibration, or dilation combined with vibration, is simple and inexpensive to manufacture, ensures convenient angle of observation for the urologist during insertion of the tool into the female urethra, and ensures an increased range of dilation diameters, and protects the proximal ends of the probe rods from deformations and concentration of stress.

Although the dilator of the invention has been described and illustrated with reference to specific examples, it is understood that the scope of application of the invention is not limited to the aforementioned examples and that any modifications are possible regarding the materials, shapes, dimensions, etc., provided these modifications do not go beyond the scope of the appended claims.

For example, lock pins 52 and 54 may be replaced by spring-loaded balls, insertable pins, screws, or other locking elements. Straight portion of rod 30 can be connected to the respective drive member by means other than thread. One rod may be stationary and another moveable. The rods of the probe may have different configurations. Although the device of the invention was shown in described in connection with female urethral dysfunctions, it may be used for treating male urethral dysfunctions. A radial handle may be connected to the rear end of shorter rod 22 for more convenient grip of the instrument during the use. Although the description contains references to specific ranges of frequencies and amplitudes, these ranges are given only as examples and may be different. Therefore the scope of the invention should be determined not by the examples given, but by appended claims and their legal equivalents.

What is claimed is:

1. A universal mechanical dilator combined with massaging action comprising:
    a probe consisting of a first rod and a second rod, said first rod having a distal end and a proximal end, said second rod having a distal end and a proximal end;
    a reciprocating drive unit having a first drive member and a second drive member, said first drive member and said second drive member reciprocating with respect to each other simultaneously and in mutually opposite directions;
    a tubular adapter between said probe and said drive unit, said adapter having a front end and a rear end, said front end of said adapter having a female thread, said proximal end of said first rod is larger in its cross section than a cross section of said second rod and has a through central opening extending in a longitudinal direction of said probe and slidingly receiving said second rod, said second rod passing through said central opening and through said adapter to said drive unit;

said proximal end of said first rod having a male thread engaging said female thread on said front end of said adapter;

said first drive member having a threaded projection, said proximal end of said second rod having a threaded opening which receives said threaded projection screwed into it for rigidly connecting said second rod to said first drive member;

said rear end of said adapter supporting means for releasably connecting said adapter to said second drive member and said second rod having means for engaging with said means for releasably connecting said adapter when said adapter is disconnected from said second drive member;

said probe having a straight portion which is slidingly received in said through opening and a bent portion which is arranged at an angle to said longitudinal direction and which is formed by said distal end of said first rod and said distal end of said second rod.

2. The mechanical urethral dilator of claim 1 wherein said bent portion of said probe is disposable, is made of a medically acceptable material, and has means for realizably connecting to said straight portion of said probe.

3. The universal mechanical dilator of claim 1 wherein said means for realisably connecting said adapter to said second drive member comprises at least one spring-loaded pin in said adapter and an annular groove in said second drive member, and said means for realisably connecting said adapter to said second drive member comprises said at least one spring-loaded pin in said adapter and an annular groove in said second rod for engaging with said pin.

4. The universal mechanical dilator of claim 1 wherein said probe is provided with first guide means on said distal end of said first rod, and second guide means on said distal end of said second rod which engages said first guide means for protecting said first rod and said second rod against deviation from said longitudinal direction.

5. The universal mechanical dilator of claim 4 wherein said first guide means is a groove made in one of said first rod and said second rod, and said second guide means is a projection which is received in said guide groove.

6. The universal mechanical dilator of claim 3 wherein said probe is provided with first guide means on said distal end of said first rod, and second guide means on said distal end of said second rod which engages said first guide means for protecting said first rod and said second rod against deviation from said longitudinal direction.

7. The universal mechanical dilator of claim 6 wherein said first guide means is a groove made in one of said first rod and said second rod, and said second guide means is a projection which is received in said guide groove.

* * * * *